United States Patent [19]

Antonik

[11] 4,340,587
[45] Jul. 20, 1982

[54] REPELLANT COMPOSITION AND METHOD OF USE

[75] Inventor: Steve J. Antonik, Mt. Prospect, Ill.

[73] Assignee: National Repellents, Inc., Mt. Prospect, Ill.

[21] Appl. No.: 103,341

[22] Filed: Dec. 13, 1979

[51] Int. Cl.$^3$ ............................................. A01N 63/02
[52] U.S. Cl. ............................... 424/95; 424/DIG. 10
[58] Field of Search .......................... 424/95, DIG. 10

[56] References Cited

U.S. PATENT DOCUMENTS 3,450,816  6/1969  Craig, Jr. et al. ..................... 424/95

Primary Examiner—Allen J. Robinson
Attorney, Agent, or Firm—Michael G. Berkman

[57] ABSTRACT

A new repellant composition, derived from natural sources and effective to repel organisms and to deter invasion by organisms such as canines, rodents, and marine life such as sharks, bony fish, and pinfish into a zone to be protected. The composition is a dispersion of or an extract of fireflies and components of fireflies, and is used by distributing the dispersion or the extract throughout a selected treatment zone.

4 Claims, No Drawings

REPELLANT COMPOSITION AND METHOD OF USE

The present invention relates to repellant compositions. More particularly, the invention is directed to compositions for repelling organisms including canines, rodents, and marine life such as sharks, bony fish and pinfish from a treatment zone from which one desires to repel such organisms or to deter invasion by such organisms.

During a research program carried out to investigate medical and related apparatus of fireflies (*Photus Pyrais*, the North American Black Firefly) and firefly dispersions, extracts, and lyophilized lanterns, bodies, and component parts of fireflies, the unexpected and remarkable discovery was made that preparations made from the fireflies exhibited the unexpected property of acting as repellants for various types of organisms. Among the organisms with respect to which the compositions have been found to be efficacious are canines, rodents, and marine life such as sharks, bony fish, and pinfish. It is expected that with continued research and investigation it will be established that the utility of the compositions as repellants will find much broader scope.

In addition to relatively simple experiments in which it was determined that firefly-derived compositions would effectively repel and deter the approach of canines and rodents, additional, more precise and controlled experiments were carried out using predatory types of marine life. The experiments are described and summarized in the following typical examples.

EXAMPLE 1

A series of tests were carried out on pinfish (*Lagodon rhomboides*). Whole, lyophilized fireflies were ground in a tissue homogenizer and suspended in seawater. Using an eight liter experimental tank containing pinfish, whole firefly "toxin" or repellant was introduced at a concentration providing one firefly per liter of seawater. The reactions of the pinfish were then observed over a period of one hour, the observations being recorded in Table I set forth below:

TABLE I

| TIME (Mins.) | OBSERVATIONS |
| --- | --- |
| 0 | distress, rapid irregular and random "darting", confusion |
| 7 | labored breathing, continued eratic swimming |
| 11 | the usual white appearance is gone, true colors returning |
| 12:45 | loss of balance |
| 15 | slow breathing, inactivity |
| 20 | increased activity, swimming fast |
| 21 | hyperventilation |
| 28 | rapid hyperventilation |
| 31 | movement of all fins, increased hyperventilation |
| 40 | no movement other than breathing |
| 45 | no change |
| 51 | loss of ability to swim, slowed down breathing |
| 56 | no change |
| 60 | no change |

EXAMPLE 2

Similar experiments were carried out at concentrations corresponding to two fireflies per liter of seawater and four fireflies per liter. The observed results are set forth below in Examples 2 and 3 in the tables below:

TABLE II

| | (Two fireflies per liter) |
| --- | --- |
| TIME (Mins.) | OBSERVATIONS |
| 0 | darting, pin-dorsal fin up, confusion |
| 7 | rapid breathing, loss of balance |
| 10 | loss of ability to swim, very rapid breathing |
| 15 | loss of ability to swim, slower breathing |
| 20 | loss of ability to swim, slow breathing, total inactivity |
| 30 | no change, slight fin movement |
| 40 | no change, slight fin movement, labored breathing |
| 50 | (same as 40 mins) |
| 55 | no change, more fin movement |
| 60 | very labored breathing, more fin movement |

TABLE III

| | (Four fireflies per liter) |
| --- | --- |
| TIME (Mins.) | OBSERVATIONS |
| 0 | Confusion, darting |
| 5 | Rapid Breathing |
| 10 | Inactive, loss of balance |
| 15 | Hard breathing, some darting |
| 20 | Hard breathing, some darting |
| 25 | Agitation, still has ability to swim |
| 30 | Agitation, still has ability to swim |
| 35 | No movement, still has ability to swim |
| 40 | No movement, still has ability to swim |
| 45 | Agitated, breathing, still has ability to swim |
| 50 | Agitated, slow breathing, has ability to swim |
| 55 | Slowed breathing, still has ability to swim |
| 60 | Inactive, slowed breathing, has ability to swim |

It is evident from a consideration of the recorded data that even at a concentration as low as one firefly per liter, the pinfish exhibited marked distress, disruption in breathing habits, color modifications, increased activity, hyperventilation, and even loss of ability to swim. The effect produced appears clearly to be a function of the concentration, more disruptive effects being evident at the higher concentration of fireflies in the seawater.

EXAMPLE 4

A similar test was carried out on the Atlantic Sharpnose Shark (*Phizoprinodon terraenoval*). The concentration of fireflies was four fireflies per liter of seawater. Again, as recorded in the table below, the shark exhibited marked reactions including hysteria, effects on respiration, chaotic movements, and rapid eye movement, all indicating a significant sensitivity to the agent introduced into the seawater.

TABLE IV

| TIME (Mins.) | OBSERVATIONS |
| --- | --- |
| 0 | massive hysteria |
| 10 | calmed down, breathing accelerated |
| 20 | circular swimming, breathing accelerated |
| 30 | No movement, rapid hyperventilation |
| 40 | No movement, rapid hyperventilation |
| 50 | Very rapid hyperventilation, chaotic movements followed by no movement |
| 60 | Very rapid hyperventilation, no movement, REM (rapid eye movement) |

It will be appreciated that the subject invention has very extensive practical use in protecting bathing zones from the invasion of objectionable sealife such as sharks. Additionally, it is clear that the compositions, which include suspensions of fresh fireflies, suspensions of lanterns of fireflies, lyophilized fireflied, and extracts of lyophilized fireflies, firefly components, and mixtures thereof may find more widespread utility in controlling and repelling many objectionable organisms including other marine life, and canines and rodents, to prevent the invasion of such organisms into a zone to be protected.

In addition to aqueous dispersion and suspension compositions, the firefly material may be incorporated in petroleum base solvents or in emulsions of aqueous-non aqueous systems for application as fluid suspensions, fogs or aerosol sprays.

What is claimed is:

1. A composition for introduction into a seawater environment of pinfish for reducing normal physical activity of the pinfish and for disrupting and adversely affecting the capability of the pinfish to function normally.

said composition comprising an aqueous dispersion of whole lyophilized ground fireflies, and said fireflies are in the seawater in a concentration of at least about one firefly per liter of seawater.

2. A composition for introduction into a seawater environment of Atlantic Sharpnose Sharks for disrupting and adversely affecting the capability of the sharks to function normally, said composition comprising an aqueous dispersion of whole lyophilized ground fireflies, and said fireflies are in the seawater in a concentration of about four fireflies per liter of seawater.

3. The method of reducing normal physical activity of pinfish and of disrupting and adversely affecting the capability of pinfish to function normally, said method comprising the steps of freeze drying and then grinding whole fireflies, and distributing the ground whole fireflies as a dispersion in seawater containing the pinfish, the concentration of ground whole fireflies being at least about one firefly per liter of seawater.

4. The method of disrupting and adversely affecting the capability of Atlantic Sharpnose Sharks to function normally, said method comprising the steps of freeze drying and grinding whole fireflies, and distributing the ground whole fireflies as a dispersion in seawater containing the sharks, the concentration of ground whole fireflies being at least about four fireflies per liter of seawater.

* * * * *